(12) United States Patent
Chen et al.

(10) Patent No.: US 11,701,087 B2
(45) Date of Patent: Jul. 18, 2023

(54) METHOD FOR HEAD AND NECK ASSESSMENT OR INTERVENTION

(71) Applicant: AmCad Biomed Corporation, Taipei (TW)

(72) Inventors: Argon Chen, Taipei (TW); Hao-Chien Wang, Taipei (TW); Chiung-Nien Chen, Taipei (TW); Pei-Lin Lee, Taipei (TW); Chin-Chung Shu, Taipei (TW); Edward Chia-Hao Liu, Taipei (TW); Shu-Ning Yu, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 571 days.

(21) Appl. No.: 16/937,196

(22) Filed: Jul. 23, 2020

(65) Prior Publication Data
US 2020/0352544 A1 Nov. 12, 2020

Related U.S. Application Data (63) Continuation-in-part of application No. 15/350,858, filed on Nov. 14, 2016, now abandoned.

(51) Int. Cl.
*A61B 8/00* (2006.01)
*A61B 8/08* (2006.01)

(52) U.S. Cl.
CPC ............... *A61B 8/40* (2013.01); *A61B 8/08* (2013.01); *A61B 8/4209* (2013.01)

(58) Field of Classification Search
CPC ..... A61B 8/08; A61B 8/40; A61B 8/42; A61B 8/4209
See application file for complete search history.

(56) References Cited

U.S. PATENT DOCUMENTS

| | | | |
|---|---|---|---|
| 5,116,344 A * | 5/1992 | Sundqvist | A61B 90/11 606/130 |
| 5,154,723 A | 10/1992 | Kubota et al. | |
| 5,320,111 A * | 6/1994 | Livingston | A61B 17/3403 606/130 |
| 5,598,269 A * | 1/1997 | Kitaevich | A61B 17/3403 356/399 |
| 5,855,582 A * | 1/1999 | Gildenberg | A61B 90/14 600/417 |
| 6,425,865 B1 | 7/2002 | Salcudean et al. | |
| 2004/0055089 A1 | 3/2004 | Dinkler et al. | |
| 2006/0233303 A1 | 10/2006 | Carlsson et al. | |
| 2006/0235435 A1 | 10/2006 | Soerensen et al. | |
| 2015/0209001 A1 | 7/2015 | Wolf et al. | |
| 2015/0297176 A1 | 10/2015 | Rincker et al. | |
| 2018/0263710 A1 | 9/2018 | Sakaguchi et al. | |
| 2018/0279992 A1 | 10/2018 | Frankel et al. | |

FOREIGN PATENT DOCUMENTS

WO WO 2016/114423 A 7/2016

* cited by examiner

*Primary Examiner* — Chao Sheng
(74) *Attorney, Agent, or Firm* — Birch, Stewart, Kolasch & Birch, LLP (57) ABSTRACT

The present disclosure provides a positioning method for head and neck assessment comprising positioning a probe to the head and neck structures of a subject according to reference planes defined by light beams.

12 Claims, 5 Drawing Sheets

METHOD FOR HEAD AND NECK ASSESSMENT OR INTERVENTION

CROSS-REFERENCE

This continuation-in-part application claims the priority under 35 U.S.C. § 120 on U.S. patent application Ser. No. 15/350,858 filed on Nov. 14, 2016, the entire contents of which are hereby incorporated by reference.

FIELD OF THE INVENTION

The present disclosure relates to a positioning method for head and neck assessment or intervention, and in particular, to a positioning method that can fix a patient's head in a position with reference to more than one desired reference planes of the patient.

BACKGROUND OF THE INVENTION

U.S. Pat. No. 6,425,865 discloses a system for medical ultrasound in which the ultrasound probe is positioned by a robot arm under the shared control of the ultrasound operator and the computer.

US 2015/0297176 A1 discloses a head frame configured for a head of a medical patient comprising support for a probe configured for imaging, therapy, or both imaging and therapy; and a neck support of rigid construction, said neck support being configured for contacting, providing rigid support for, a neck of said patient.

SUMMARY OF THE INVENTION

One aspect of the present disclosure is to provide a method of positioning a probe to head and neck structures of a subject, comprising: providing a head fixation assembly to dispose a subject's head and neck; defining a first reference plane by a guide extending upwards to the normal direction of the subject's body; defining a second reference plane by a first light beam which passes through a longitudinal axis fitting into the ear canal of the subject and delineate a first line; defining a third reference plane by a second light beam which represent a medial plane of the subject and delineate a second line; and positioning the subject's head and neck structures according to a point where the first line and the second line cross.

In a particular embodiment, wherein a probe is directed to be aligned with the extension of first line and the second line in a longitude direction of the probe.

In a particular embodiment, wherein the head fixation assembly comprises a main body attached to a base having two upwardly extending lateral ends and an ear aligning member for aligning with the opening of ear canal of the subject configured on an inner side of each of the lateral ends; the main body has two upwardly extending lateral ends; and the guide extends upward and slightly inward from each of the lateral ends.

In a particular embodiment, wherein the head fixation assembly is slidably attached to the base.

In a particular embodiment, wherein the head fixation assembly further comprises a pillow member for supporting the head of the subject, disposed on the main body between its lateral ends.

In a particular embodiment, wherein the pillow member is adapted for adjusting a tilt angle of the head of the subject with respect to a transverse plane of the subject.

In a particular embodiment, wherein the first reference plane is a Frankfort horizontal plane of the subject.

In a particular embodiment, the method is used in the assessment of obstructive sleep apnea by ultrasound imaging.

In a particular embodiment, wherein the guide includes a line representing the first reference plane, or wherein the guide includes a transparent substrate extending upward and slightly inward from each of the lateral ends.

In a particular embodiment, wherein the guide is configured such that the line representing the first reference plane is orthogonal to both a longitudinal axis of a protruding part of an ear aligning member aligned with the opening of ear canal of the subject and the base and the method further comprising: fitting the protruding part of the ear aligning member into an ear canal of the subject and then aligning an end point of the line of the guide with the most inferior aspect of the infraorbital rim of the subject.

In a particular embodiment, wherein the second reference plane forms a HM plane of the subject and the method is used in positioning a probe to the HM plane of the subject.

Another aspect of the preset disclosure is to provide a method of positioning a probe to head and neck structures of a subject, comprising: providing a head fixation assembly to dispose a subject's head and neck, wherein the head fixation assembly comprises an ear aligning member for aligning with the opening of ear canal of the subject; defining a first reference plane by a guide extending upwards to the normal direction of the subject's body, wherein the guide includes a line representing the first reference plane and the first reference plane is a Frankfort horizontal plane of the subject and wherein the guide is configured such that the line representing the first reference plane is orthogonal to both a longitudinal axis of a protruding part of the ear aligning member aligned with the opening of an ear canal of the subject and the base; fitting the protruding part of the ear aligning member into the ear canal of the subject and then aligning an end point of the line of the guide with the most inferior aspect of the infraorbital rim of the subject; defining a second reference plane by a first light beam which passes through a longitudinal axis fitting into the ear canal of the subject and delineate a first line, wherein the second reference plane defined by the first light beam represents a hyoid-external auditory meatus plane of the subject; defining a third reference plane by a second light beam which represent a medial plane of the subject and delineate a second line; and positioning the subject's head and neck structures according to a point where the first line and the second line cross, wherein a probe is directed to be aligned with the extension of first line and the second line in a longitude direction of the probe.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The foregoing summary, as well as the following detailed description of the disclosure, will be better understood when read in conjunction with the appended drawing. In the drawings.

DESCRIPTION OF THE INVENTION

Unless defined otherwise, all technical and scientific terms used herein have the same meaning as commonly understood by a person skilled in the art to which this disclosure belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present disclosure provides a positioning apparatus for head and neck assessment or intervention of a subject. The positioning apparatus comprises a base, a head fixation assembly, a first connector, a first light transmitter, and a holder assembly. The head fixation assembly includes a main body, a guide representing a first reference plane of the subject, and an ear aligning member. The main body is attached to the base and has two upwardly extending lateral ends. The guide extends upward and slightly inward from each of the lateral ends. The ear aligning member is to be aligned with the opening of ear canal of the subject. The ear aligning member is configured on an inner side of each of the lateral ends. The first connector has a first end and an opposite second end. The first end is pivotally connected to the lateral end of the main body on an outer side at a first pivot point. Accordingly, the first connector is rotatable with respect to the first pivot point. The first light transmitter is able to project a first light beam, and is configured at the second end of the first connector, such that the first light beam defines a second reference plane passing through the first pivot point. The holder assembly includes an adjustable first stand, and a holder for holding a medical device for the assessment or intervention. The first stand is secured to the base, and the holder is pivotally connected to the first stand.

The positioning apparatus of the present disclosure is generally designed for head and neck assessment or intervention of a subject in a lying down or leaning backward position. Therefore, the base of the positioning apparatus is preferably a plate-like base which is adapted to flat against and/or be fixed on a bed. According to one embodiment of the present disclosure, the base is configured with one or more belts on a lateral side thereof, which may be used to fix the base to the bed.

According to certain embodiments of the present disclosure, the ear aligning member has a protruding part for fitting into the ear canal of the subject. Preferably, the first pivot point lies on a longitudinal axis of the protruding part of the ear aligning member. In some other embodiments, the ear aligning member includes a third light transmitter which projects a linear light beam (e.g., a laser transmitter which projects a linear laser beam) for aligning with the ear canal of the subject. Preferably, the first pivot point lies on an imaginary line extended from said linear light beam.

According to certain embodiments of the present disclosure, the main body of the head fixation assembly is slidably attached to the base.

In certain embodiments of the present disclosure, the guide includes a line representing the first reference plane. In some embodiments, the guide includes a transparent substrate extending upward and slightly inward from each of the lateral ends. According to one specific embodiment of the present disclosure, the transparent substrate is marked with a line representing the first reference plane. In another embodiment, the transparent substrate is projected with a light beam which serves as a line representing the first reference plane.

According to the present disclosure, the guide is preferably retractable in length. For example, the transparent substrate may be strip-like and be adapted to slide into and out of the main body, such that the guide may be in part pushed into the lateral end of the main body for the convenience of placement of the subject's head on the main body between its lateral ends, and may be later drawn out for aligning an end point of the line with certain reference point on the subject's head when an operator is to adjust the position of the subject's head with reference to the line of the guide.

According to certain embodiments of the present disclosure, the ear aligning member and the first connector are coaxially connected to the main body, such that the first pivot point, where the first connector is pivoted to the lateral end of the main body, lies on the longitudinal axis of the protruding part of the ear aligning member. In some embodiments, the ear aligning member and the first connector may be synchronously slidable relative to the lateral end of the main body. This allows an operator to adjust the position of the ear aligning member for fitting the protruding part of the ear aligning member into an ear canal of the subject.

According to certain embodiments of the present disclosure, the head fixation assembly further includes a pillow member for supporting the head of the subject, the pillow member being disposed on the main body between its lateral ends. Preferably, the pillow member is adapted for adjusting a tilt angle of the head of the subject with respect to a transverse plane of the subject. In addition, the pillow member may be replaceable.

In some embodiments of the present disclosure, the guide is configured such that the line representing the first reference plane is orthogonal to both the longitudinal axis of the protruding part of the ear aligning member and the base. In other words, the first reference plane passes through the first pivot point, and thus, the opening of ear canal of the subject. According to certain preferred embodiments of the present disclosure, the first reference plane is a Frankfort horizontal plane of the subject. The Frankfort horizontal plane may be defined as a line drawn from (the superior aspect of) the external auditory canal to the most inferior aspect of the infraorbital rim. Accordingly, in such embodiments, an operator can use the guide(s) to assist the positioning of the head of the subject, by fitting the protruding part(s) of the ear aligning member(s) into the ear canal(s) of the subject and then aligning an end point of the line of the guide(s) with the most inferior aspect of the infraorbital rim(s) of the subject, to adjust the subject's head (for example, adjusting the tilt angle of the head by using the pillow member) to a position where a Frankfort horizontal plane of the subject is orthogonal to the base.

According to certain preferred embodiments, the first stand includes a first arm extending upward from the base to an upper end; a second arm connected to the upper end of the first arm at a right angle and extending along a direction parallel to the medial line of the head fixation assembly to an inferior end; a third arm connected to the inferior end of the second arm at a right angle and extending along a direction perpendicular to the medial line of the head fixation assembly to an medial end; and a fourth arm connected to the medial end of the third arm at a right angle and extending downward to a lower end. Preferably, the length of each arm is adjustable. In one embodiment, the holder is pivotally connected to the lower end of the fourth arm. According to certain embodiments of the present disclosure, the holder is customized or adjustable for different assessment/intervention purposes. For example, some holders may be suitable for "transverse ultrasound scanning", and other holders may be suitable for "sagittal ultrasound scanning". Alternatively, for example, the holder may be rotatable with respect to the fourth arm for the switch between a "transverse ultrasound scanning" mode and a "sagittal ultrasound scanning" mode.

According to one embodiment of the present disclosure, considering individual differences, the ear aligning member is adjustable in the sense that its distance to the ear of the subject can be adjusted.

According to certain embodiments of the present disclosure, the positioning apparatus further comprises a second light transmitter. The second light transmitter is able to project a second light beam which defines a third reference plane. In some preferred embodiments, the third reference plane represents a medial plane of the subject. In one embodiment of the present disclosure, the second light transmitter is configured on the fourth arm of the first stand on a side facing the head fixation assembly.

In certain embodiments of the present disclosure, the positioning apparatus further comprises a second stand, a second connector, and a second light transmitter. The second stand is secured to the base and extends upward to an upper end. The second connector has a first end and an opposite second end. The first end of the second connector is pivotally connected to the upper end of the second stand at a second pivot point, such that the second connector is rotatable with respect to the second pivot point. The second light transmitter is able to project a second light beam and is configured at the second end of the second connector, such that the second light beam defines a third reference plane passing through the second pivot point. In one embodiment of the present disclosure, the second stand is secured to the base at a securing point where a medial line of the head fixation assembly passes through. In such embodiment, the third reference plane may be a medial plane of the subject.

However, in some other embodiments of the present disclosure, instead of securing to the base, the second stand is constructed as a separate module from the positioning apparatus, allowing an operator to set up the second stand and the second light transmitter thereon at a desired location where the second light beam is properly projected onto the subject to delineate a third reference plane.

Furthermore, alternatively, the second light transmitter may be configured on the fourth arm (e.g., at a side facing the head fixation assembly) of the above-mentioned first stand. Preferably, the second light transmitter is adjustable with respect to the fourth arm, so that an operator can adjust the third reference plane defined by the second light beam.

According to certain embodiments of the present disclosure, the first connector and/or the second connector is retractable in length, so that an operator can adjust the first light transmitter and/or the second light transmitter to a desired location.

Preferably, the first light transmitter is a laser transmitter which projects a linear laser beam, and the second light transmitter is also a laser transmitter which projects a linear laser beam.

According to present disclosure, the first light beam defining the second reference plane and the second light beam defining the third reference plane may have a cross-point on the subject, representing a desired point where the assessment or intervention is to be performed. For example, an operator can move the medical device to direct to said cross-point using the adjustable first stand of the holder assembly, to perform a specific assessment or intervention.

Accordingly, the first stand preferably provides some degree of freedom of movement of the medical device, such that an operator can move the medical device to an appropriate position for the assessment or intervention, through a computer controlled system or manually.

In some embodiments of the present disclosure, the holder assembly further includes a motor for rotating the holder with respect to the first stand. Such embodiments are especially useful in 3D ultrasound imaging which requires a range of scanning. The movement/rotation patterns of the holder may be controlled by a computer program.

According to certain embodiments of the present disclosure, the holder comprises a frame part and a holding part, the frame part being pivotally connected to the first stand, the holding part being pivotally connected to the frame part and adapted for holding the medical device. In one embodiment, the holder further comprises a motor for rotating the holding part with respect to the frame part, such that the tip of the medical device can be moved toward a superior direction and/or an inferior direction of the subject. Further, the holding part may be coaxially rotatable with respect to the frame part for the switch between a "transverse ultrasound scanning" mode and a "sagittal ultrasound scanning" mode, in the case of ultrasound scanning, but not limited thereto. In another embodiment, the holding part includes a cushioning element for cushioning the movement of the medical device relative to the holding part.

In certain preferred embodiments of the present disclosure, the holder assembly further includes a cushioning element for cushioning the movement of the medical device relative to the holder. This makes it less uncomfortable when the medical device is required to be held close against and/or move around an assessment area on the subject.

According to one preferred embodiment of the present disclosure, the positioning apparatus is used in the assessment of obstructive sleep apnea of the subject by ultrasound imaging. In such embodiment, the second reference plane may be a plane passing through the hyoid bone and the external auditory meatus in addition to the ear canal (referred as HM plane herein), and the third reference plane may be a medial plane of the subject.

According to the present disclosure, the positioning apparatus can be used in at least the following assessments or interventions: ultrasound-guided interventions (e.g., puncture, injection, biopsy, and nerve block), and ultrasound imaging of peripheral arteriovenous of neck, carotid artery, cervical lymph node, thyroid, parathyroid or parotid.

The present disclosure also provides a method of positioning a probe to head and neck structures of a subject, comprising: providing a head fixation assembly to dispose a subject's head and neck; defining a first reference plane by a guide extending upwards to the normal direction of the subject's body; defining a second reference plane by a first light beam which passes through a longitudinal axis fitting into the ear canal of the subject and delineate a first line;

defining a third reference plane by a second light beam which represent a medial plane of the subject and delineate a second line; and positioning the subject's head and neck structures according to a point where the first line and the second line cross.

The term used herein "head and neck structures" encompasses a subject's midline palpable anterior neck structures, including but not limited to hyoid bone, angle of the mandible, thyroid cartilage, cricoid cartilage, and Chassaignac tubercle. Thus the method according to the present disclosure can be a method of positioning a probe to, for example, hyoid bone, angle of the mandible, thyroid cartilage, cricoid cartilage, or Chassaignac tubercle of a subject.

Hence in one embodiment, the second reference plane forms a HM plane of the subject and the method is used in positioning a probe to the hyoid bone of the subject.

According to the present disclosure, the positioning method can be used in at least the following assessments or interventions: ultrasound-guided interventions (e.g., puncture, injection, biopsy, and nerve block), and ultrasound imaging of peripheral arteriovenous of neck, carotid artery, cervical lymph node, thyroid, parathyroid or parotid.

Certain preferred embodiments of the present disclosure are described below.

Figure 1:
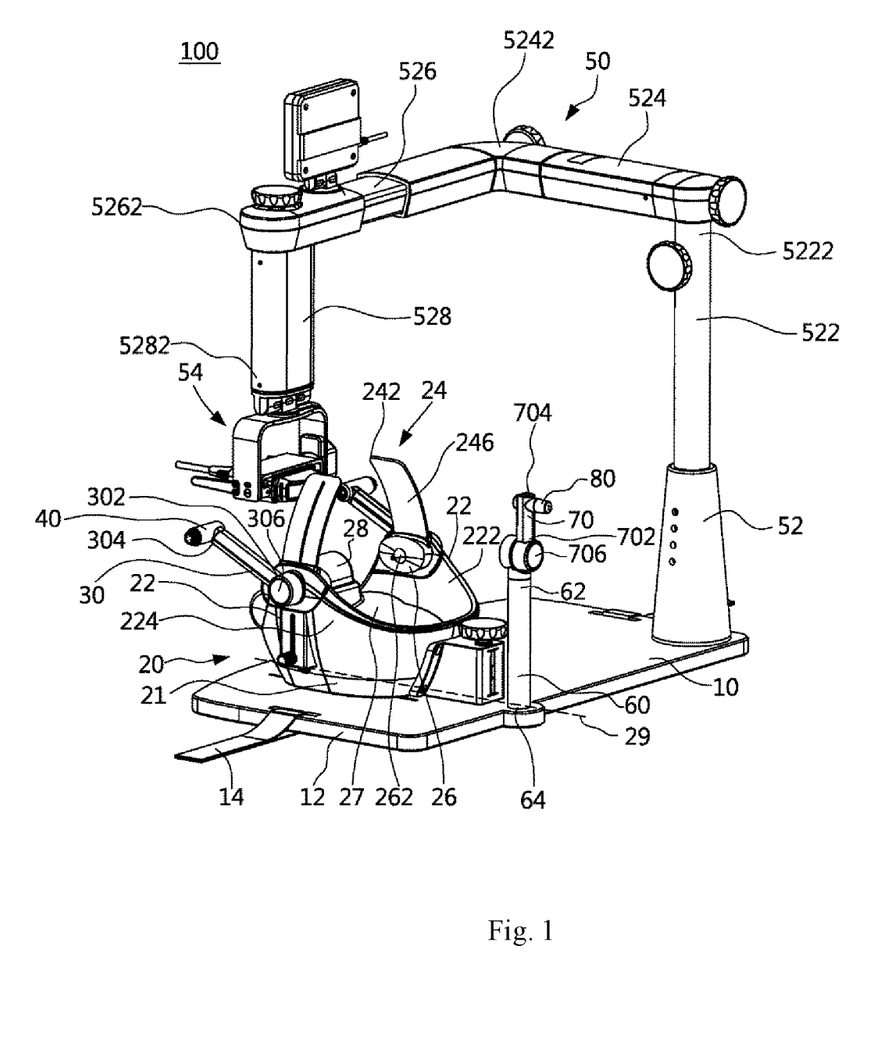
FIG. 1 is a perspective view of a positioning apparatus according to the present disclosure.
Figure 2:
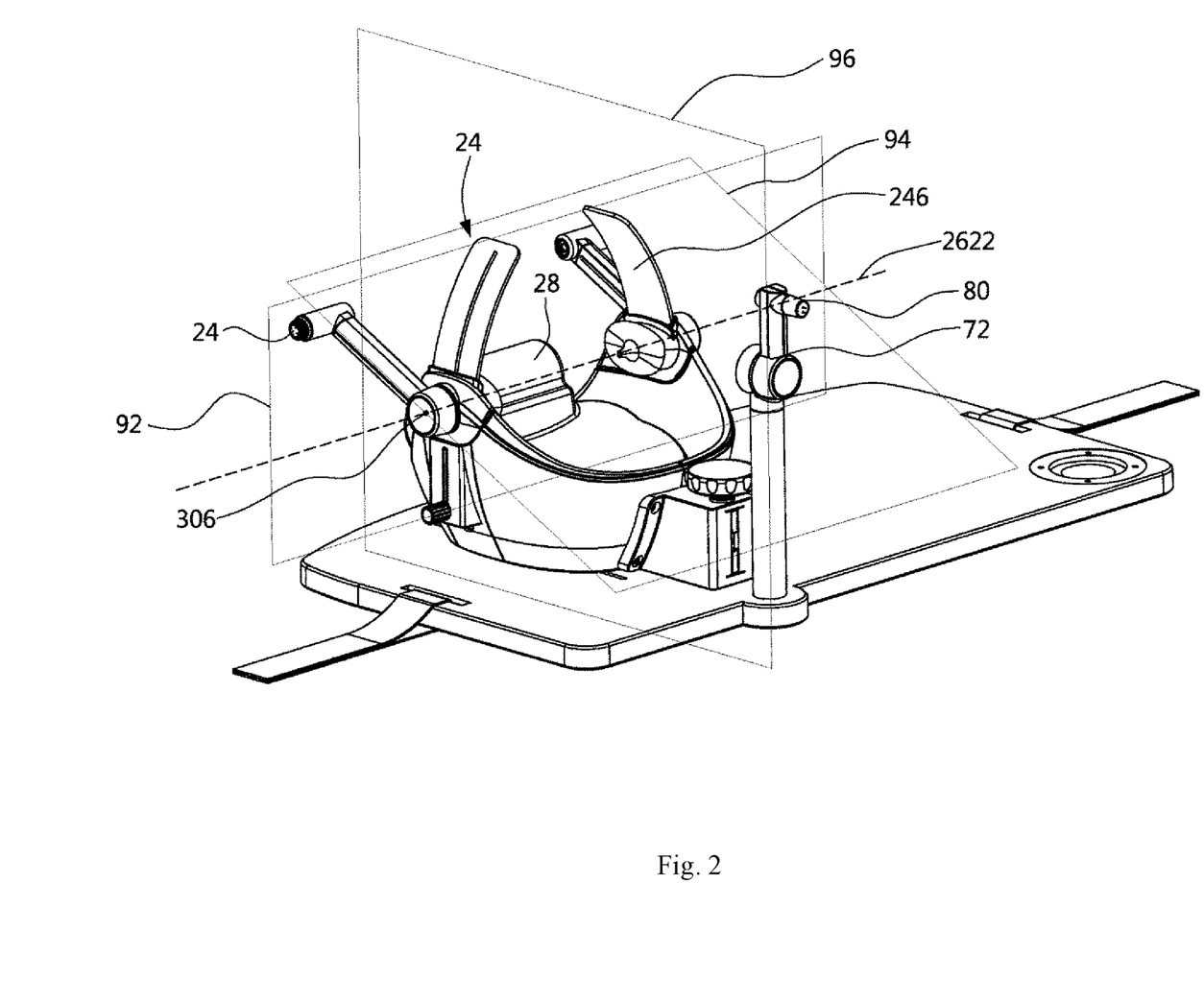
FIG. 2 is a schematic drawing illustrating the first, second and third reference planes.
Figure 3:
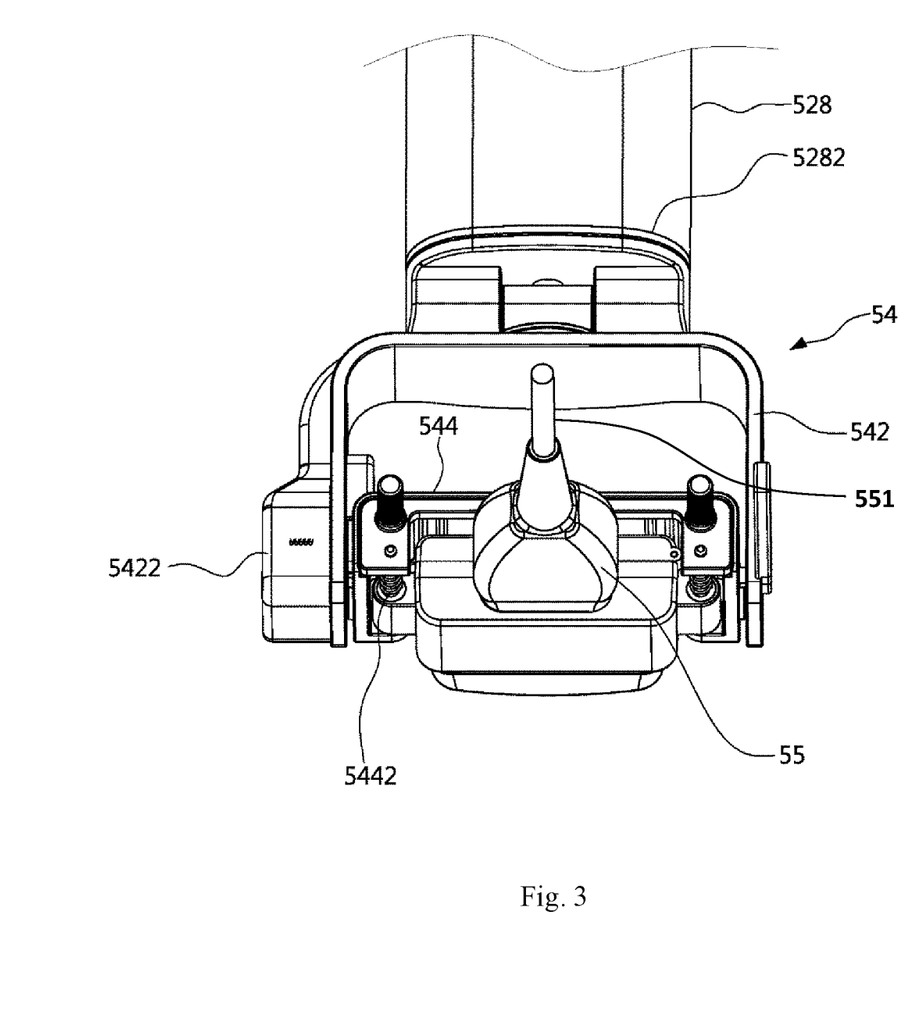
FIG. 3 is a perspective view of a holder of a positioning apparatus according to the present disclosure.

With reference to FIGS. 1-3, provided is a positioning apparatus 100 for head and neck assessment or intervention of a subject. The positioning apparatus 100 comprises a base 10, a head fixation assembly 20, a first connector 30, a first light transmitter 40, a holder assembly 50, a second stand 60, a second connector 70, and a second light transmitter 80. The head fixation assembly 20 includes a main body 21, a guide 24 representing a first reference plane 92 of the subject, and an ear aligning member 26. The main body 21 is attached to the base 10 and has two upwardly extending lateral ends 22. The guide 24 extends upward and slightly inward from each of the lateral ends 22. The ear aligning member 26 is configured on an inner side 222 of each of the lateral ends 22 and has a protruding part 262 for fitting into the ear canal of the subject. The head fixation assembly 20 may further include a pillow member 28 for supporting the head of the subject, the pillow member 28 being disposed on the main body 21 between its lateral ends 22. Preferably, the pillow member is 28 adapted for adjusting a tilt angle of the head of the subject with respect to a transverse plane of the subject.

The first connector 30 has a first end 302 and an opposite second end 304. The first end 302 is pivotally connected to the lateral end 22 of the main body 21 on an outer side 224 at a first pivot point 306 lying on a longitudinal axis 2622 (see FIG. 2) of the protruding part 262 of the ear aligning member 26. The first light transmitter 40 is able to project a first light beam, and is configured at the second end 304 of the first connector 30, such that the first light beam defines a second reference plane 94 (see FIG. 2) passing through the first pivot point 306. The holder assembly 50 includes an adjustable first stand 52, and a holder 54 for holding a medical device 55 for the assessment or intervention (see FIG. 1 and FIG. 3). The first stand 52 is secured to the base 10, and the holder 54 is pivotally connected to the first stand 52. The second stand 60 is secured to the base 10 and extends upward to an upper end 62. The second connector 70 has a first end 702 and an opposite second end 704. The first end 702 of the second connector 70 is pivotally connected to the upper end 62 of the second stand 60 at a second pivot point 706. The second light transmitter 80 is able to project a second light beam and is configured at the second end 704 of the second connector 70, such that the second light beam defines a third reference plane 96 passing through the second pivot point 706. In this embodiment, the second stand 60 is secured to the base 10 at a securing point 64 where a medial line 29 of the head fixation assembly 20 passes through. As such, the third reference plane 96 may be a medial plane of the subject if the second connector 70 is in an upright position. In addition, the first stand 52 includes a first arm 522 extending upward from the base 10 to an upper end 5222; a second arm 524 connected to the upper end 5222 of the first arm 522 at a right angle and extending along a direction parallel to the medial line 29 of the head fixation assembly 20 to an inferior end 5242; a third arm 526 connected to the inferior end 5242 of the second arm 524 at a right angle and extending along a direction perpendicular to the medial line 29 of the head fixation assembly 20 to an medial end 5262; and a fourth arm 528 connected to the medial end 5262 of the third arm 526 at a right angle and extending downward to a lower end 5282. The holder 54 includes a frame part 542 and a holding part 544, the frame part 542 being pivotally connected to the lower end 5282 of the fourth arm 528 of the first stand 50, the holding part 544 being pivotally connected to the frame part 542 and adapted for holding the medical device 55 (see FIG. 3). In one embodiment, the medical device 55 of the present disclosure is an ultrasound transducer, wherein the ultrasound transducer has a probe 551 disposed along a longitude direction of the medical device 55. The holder 54 further includes a motor 5422 for rotating the holding part 544 with respect to the frame part 542. The holding part 544 includes a cushioning element 5442 for cushioning the movement of the medical device 55 relative to the holding part 544. The angle of the medical device 55 relative to the subject's body can be adjusted via the adjustment of the holding part 544.

Figure 4:
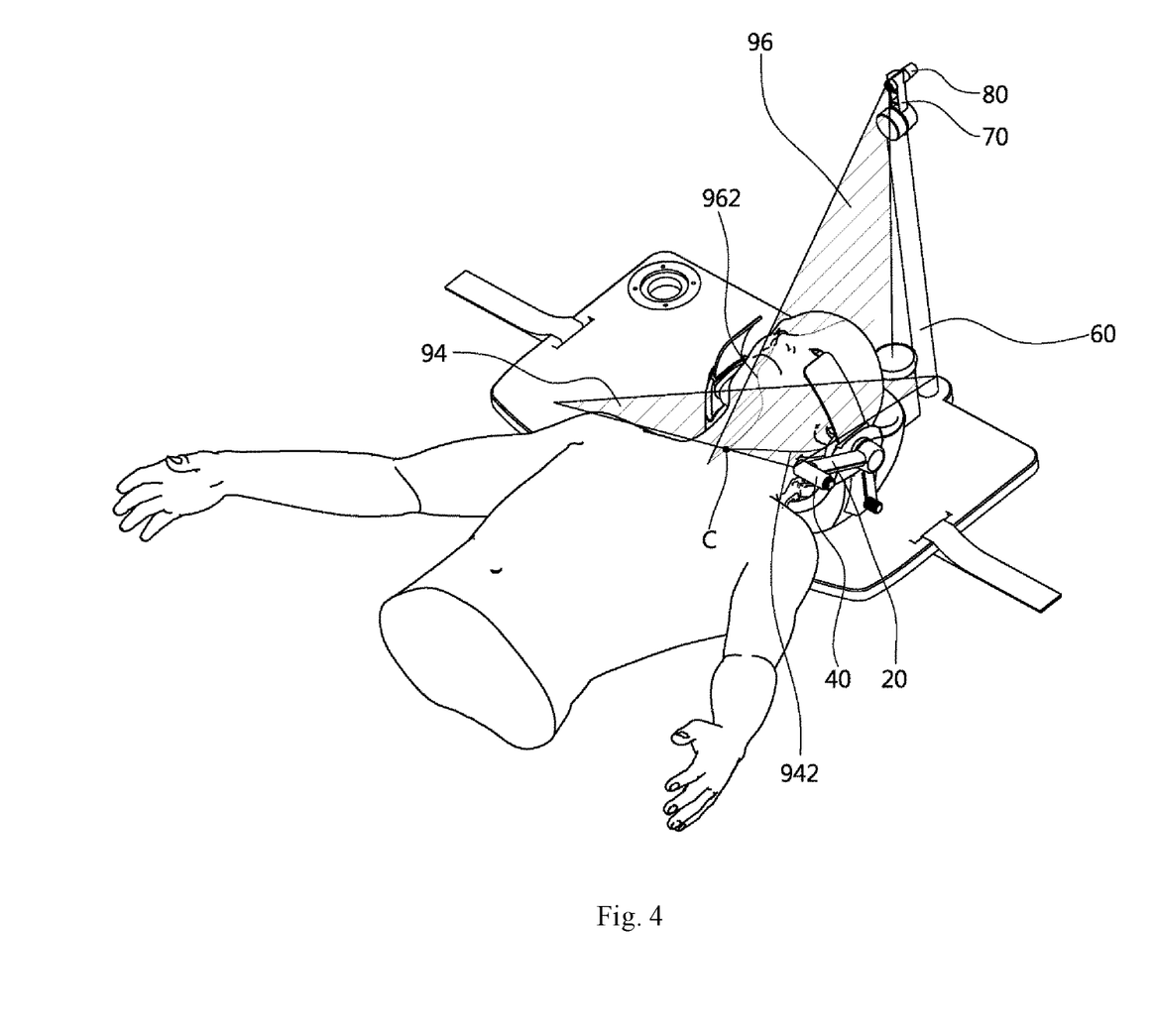
FIG. 4 illustrates the use of a positioning apparatus according to the present disclosure in the assessment of obstructive sleep apnea of a subject by ultrasound imaging.
Figure 5:
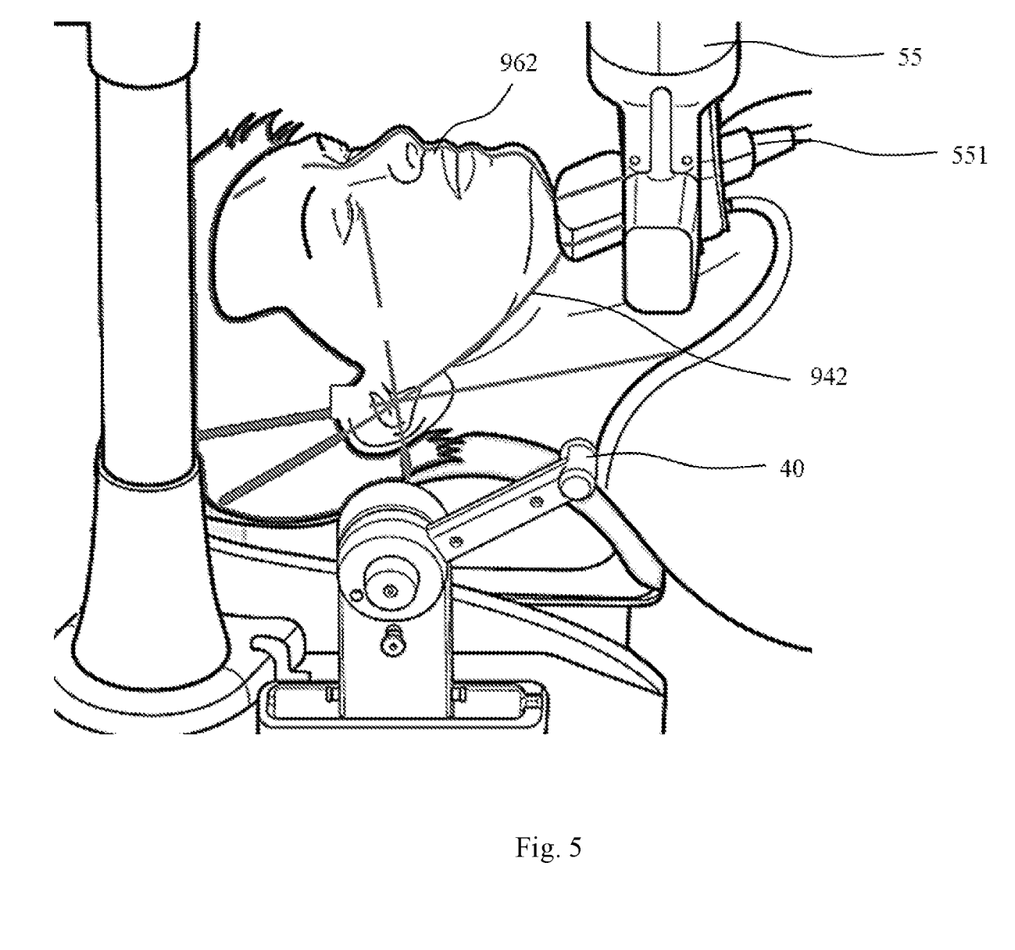
FIG. 5 is an illustrative view of the positioning of head and neck structures of a subject and the alignment of probe and the lines.

FIG. 4 is a perspective drawing illustrating the use of a positioning apparatus according to the present disclosure in the assessment of obstructive sleep apnea of a subject by ultrasound imaging. FIG. 5 is an illustrative view of the positioning of the head and neck structures of a subject and the alignment of probe and the lines. According to the present disclosure, the head and neck structures encompass at least a subject's hyoid bone, angle of the mandible, thyroid cartilage, cricoid cartilage, and Chassaignac tubercle. Thus the method according to the present disclosure can be a method of positioning a probe to, for example, hyoid bone, angle of the mandible, thyroid cartilage, cricoid cartilage, or Chassaignac tubercle of a subject.

Referring to FIG. 4, FIG. 5 together with FIGS. 1-2, after the subject lies down with his/her head placed in the head fixation assembly 20 on the pillow member 28, and the positions of both ear aligning members 26 is adjusted to align a respective opening of ear canal of the subject, the tilt angle of the subject's head may be first adjusted with the aid of the guide 24 through the pillow member 28 such that the subject's Frankfort horizontal plane (represented by the first reference plane 92) is parallel to the normal direction the base (and thus perpendicular to the surface of the examination bed (not shown)). Subsequently, the operator may identify the location of the subject's hyoid bone by hand and adjust the first connector 30 accordingly such that the second reference plane 94 defined by the first light beam from the first light transmitter 40 represents the HM plane of the subject and that the first light beam delineates a first line 942 (passing through the identified location of the hyoid bone) on the subject's surface. Further, the second connector 70 may be adjusted to an upright position such that the third reference plane 96 defined by the second light beam from the second light transmitter 80 represents the medial plane of the subject and that the second light beam delineates a second line 962 on the subject's surface. The first and second lines 942 and 962 would cross at a point C on the subject's surface. Then, the operator may adjust the adjustable first stand 52 to direct the tip of an ultrasound probe to the point C for scanning the retroglossal region and the retropalatal region of the subject. In another example, for thyroid examination, the operator may identify the location of the subject's thyroid cartilage instead, and adjust the first connector 30 accordingly such that the second reference plane 94 defined by the first light beam from the first light transmitter 40 represents a thyroid cartilage-external auditory meatus plane of the subject and that the first light beam delineates a first line 942 (passing through the identified location of the thyroid cartilage) on the subject's surface. As such, the point C where the first and second lines 942 and 962 cross represents a central point of the subject's thyroid cartilage toward which the operator may adjust the adjustable first stand 52 to direct the tip of an ultrasound probe for thyroid examination. In another example, for the examination of upper airway, the operator may identify the location of the subject's HM plane and adjust the first connector 30 accordingly such that the second reference plane 94 defined by the first light beam from the first light transmitter 40 represents the HM plane of the subject and that the first light beam delineates a first line 942 on the subject's body surface. Further, the second connector 70 may be adjusted to an upright position such that the third reference plane 96 defined by the second light beam from the second light transmitter 80 represents the medial plane of the subject and that the second light beam delineates a second line 962 on the subject's surface. The first and second lines 942, 962 would cross at a point C on the subject's surface. Subsequently, the probe 551 of the ultrasound transducer is directed to a position on the subject's body where a longitude direction of the probe 551 is positioned to align with the extension of the first line and the second line 942, 962, respectively. As a consequence, the longitude direction of the probe 551 is in a position on both of the second reference plane and third reference plane 94, 96. Accordingly, as the probe 551 is directed to be aligned with the light beams, the probe 551 of the ultrasound transducer is positioned against the hyoid bone for further therapeutic procedure.

In certain preferred embodiments of the present disclosure, the holder assembly further includes a cushioning element for cushioning the movement of the medical device relative to the holder. This makes it less uncomfortable when the medical device is required to be held close against and/or move around an assessment area on the subject.

It is believed that a person of ordinary knowledge in the art where the present disclosure belongs can utilize the present disclosure to its broadest scope based on the descriptions herein, either alone or in combination of the embodiments, with no need of further illustration. Therefore, the descriptions and claims as provided should be understood as of demonstrative purpose instead of limitative in any way to the scope of the present disclosure.

We claim:

1. A method of positioning a probe to head and neck structures of a subject, comprising:
providing a head fixation assembly to dispose a subject's head and neck;
defining a first reference plane by a guide extending upwards to the normal direction of the subject's body;
defining a second reference plane by a first light beam which passes through a longitudinal axis fitting into an ear canal of the subject and delineate a first line;
defining a third reference plane by a second light beam which represent a medial plane of the subject and delineate a second line; and
positioning the subject's head and neck structures according to a point where the first line and the second line cross;
wherein the probe is directed to be aligned with both an extension of the first line and an extension of the second line in a longitude direction of the probe.

2. The method of claim 1, wherein the first reference plane is a Frankfort horizontal plane of the subject.

3. The method of claim 1, which is used in the assessment of obstructive sleep apnea by ultrasound imaging.

4. The method of claim 1, wherein the second reference plane forms a HM plane of the subject and the method is used in positioning the probe to the hyoid bone of the subject.

5. The method of claim 1, wherein the guide includes a line representing the first reference plane, or wherein the guide includes a transparent substrate extending upward and inward from each of the lateral ends.

6. The method of claim 5, wherein the guide is configured such that the line representing the first reference plane is orthogonal to both a longitudinal axis of a protruding part of an ear aligning member aligned with the opening of the ear canal of the subject and the base and the method further comprising: fitting the protruding part of the ear aligning member into the ear canal of the subject and then aligning an end point of the line of the guide with the most inferior aspect of the infraorbital rim of the subject.

7. The method of claim 1, wherein the head fixation assembly comprises a main body attached to a base having two upwardly extending lateral ends and an ear aligning member for aligning with the opening of the ear canal of the subject configured on an inner side of each of the lateral ends; the main body has two upwardly extending lateral ends; and the guide extends upward and inward from each of the lateral ends.

8. The method of claim 7, wherein the head fixation assembly is slidably attached to the base.

9. The method of claim 7, wherein the head fixation assembly further comprises a pillow member for supporting the head of the subject, disposed on the main body between its lateral ends.

10. The method of claim 9, wherein the pillow member is adapted for adjusting a tilt angle of the head of the subject with respect to a transverse plane of the subject.

11. A method of positioning a probe to head and neck structures of a subject, comprising:
providing a head fixation assembly to dispose a subject's head and neck, wherein the head fixation assembly comprises an ear aligning member for aligning with the opening of an ear canal of the subject;
defining a first reference plane by a guide extending upwards to the normal direction of the subject's body, wherein the guide includes a line representing the first reference plane and the first reference plane is a Frankfort horizontal plane of the subject and wherein the guide is configured such that the line representing the first reference plane is orthogonal to both a longitudinal axis of a protruding part of the ear aligning member aligned with the opening of the ear canal of the subject and the base;
fitting the protruding part of the ear aligning member into the ear canal of the subject and then aligning an end point of the line of the guide with the most inferior aspect of the infraorbital rim of the subject;

defining a second reference plane by a first light beam which passes through a longitudinal axis fitting into the ear canal of the subject and delineate a first line, wherein the second reference plane defined by the first light beam represents a hyoid-external auditory meatus plane of the subject;

defining a third reference plane by a second light beam which represent a medial plane of the subject and delineate a second line; and positioning the subject's head and neck structures according to a point where the first line and the second line cross, wherein the probe is directed to be aligned with both an extension of the first line and an extension of the second line in a longitude direction of the probe.

12. The method of claim 11, wherein the second reference plane forms a HM plane of the subject and the method is used in positioning the probe to the hyoid bone of the subject.

\* \* \* \* \*